United States Patent [19]

Phillips et al.

[11] Patent Number: 4,474,789

[45] Date of Patent: Oct. 2, 1984

[54] (TRICHLOROMETHYL)PYRIDINE COMPOUNDS USEFUL FOR PROMOTING GROWTH AND/OR IMPROVING FEED UTILIZATION EFFICIENCY IN RUMINANTS

[75] Inventors: Dorothy J. Phillips; Jack M. Tadman, both of Midland, Mich.

[73] Assignee: The Dow Chemical Company, Midland, Mich.

[21] Appl. No.: 340,153

[22] Filed: Jan. 18, 1982

[51] Int. Cl.$^3$ ............................................. A61K 31/44
[52] U.S. Cl. .................................................... 424/263
[58] Field of Search ........................................ 424/263

[56] References Cited

U.S. PATENT DOCUMENTS 3,135,594  6/1964  Goring ...................................... 71/11

Primary Examiner—Frederick E. Waddell

[57] ABSTRACT

(Trichloromethyl)pyridine compounds improve growth rate and feed utilization efficiency when orally administered to ruminants in amounts sufficient to cause any one or more of the following effects: (1) increase the amount of propionate relative to acetate present in the rumen, (2) decrease the methane concentration in the rumen by the inhibition of methanogenesis and (3) increase the amino acid nitrogen level in the rumen.

18 Claims, No Drawings

(TRICHLOROMETHYL)PYRIDINE COMPOUNDS USEFUL FOR PROMOTING GROWTH AND/OR IMPROVING FEED UTILIZATION EFFICIENCY IN RUMINANTS

BACKGROUND OF THE INVENTION

The present invention relates to (trichloromethyl)pyridine compounds useful for improving the feed utilization efficiency and for promoting growth in ruminant animals.

The agricultural industry is constantly in search of methods to improve the growth rate and the feed utilization efficiency in agriculturally important animals particularly ruminant animals.

It is well known that the efficiency of feed utilization by a ruminant animal can be monitored by chemical analysis of the rumen fermentation. Altering the carbohydrate fermentation to increase the concentration of propionate relative to acetate results in an improvement in growth rate and/or feed utilization efficiency in ruminant animals. In vitro rumen fermentation tests that measure the volatile fatty acid (VFA) production are indicators in determining if compounds are active in vivo in causing an increase in propionate levels relative to acetate levels. See. U.S. Pat. Nos. 3,937,836; 3,928,571; 4,141,907; 3,839,557; and 3,794,732.

It is also known that inhibiting methanogenesis in the rumen results in an apparent decrease in gaseous loss of methane via eructation and a shift toward producing more desirable volatile fatty acids for growth of the animal, especially propionic and butyric acids. See U.S. Pat. Nos. 3,745,221; 3,615,649; and 3,862,333.

Altering nitrogen metabolism in the rumen, such as, by inhibiting amino acid deamination, enables the ruminant animal to utilize protein or amino acids more efficiently. See U.S. Pat. No. 3,862,333.

The compounds of the present invention cause a substantially complete inhibition of the formation of methane in the rumen. This substantially complete inhibition of methanogenesis in the rumen is an advantage that the present compounds possess over commercially available products, such as monensin, which cause only a partial decrease in the methane concentration in the rumen.

U.S. Pat. No. 3,135,594 discloses (trichloromethyl)pyridine compounds useful as nitrification inhibitors for conserving soil nitrogen and for supplying the soil nitrogen requirements for plant nutrition.

Heretofore, the compounds of the present invention have not been disclosed as compounds which improve growth rate and/or feed utilization efficiency in ruminant animals.

SUMMARY OF THE INVENTION

Briefly, in accordance with the present invention, the growth rate and/or feed utilization efficiency of ruminant animals having a developed rumen function is improved by orally administering to the ruminant a rumen-modifying amount of a compound corresponding to the formula

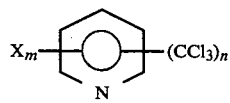

wherein
n represents 1, 2 or 3;
each X independently represents methyl or chloro;
m represents 0, 1, 2, 3 or 4 with the proviso that n+m is not greater than 5; and
physiologically acceptable salts thereof, whereby the propionate level in the rumen of said ruminant, relative to the acetate, is increased; the methanogenesis in the rumen is decreased; and the amino acid nitrogen content in the rumen is increased.

Additionally, the present invention relates to a rumen-modifying composition comprising at least one active compound of Formula I in admixture with a physiologically acceptable adjuvant therefor, said active compound being present in an amount of at least 1 ppm by weight. The compositions are typically animal feeds.

DETAILED DESCRIPTION OF THE EMBODIMENTS

The term "rumen-modifying amount", when used herein, refers to an amount of active compound, which, when administered orally to a ruminant, produces any one or more of the following effects: (1) an increase in the amount of propionate relative to acetate present in the rumen of the animal, (2) a decrease in the methane concentration in the rumen by inhibiting methanogenesis and (3) an increase in the amino acid nitrogen level in the rumen. These effects, either singly or in combination, improve feed utilization efficiency and/or growth rate in ruminants.

The term "ruminant" when used herein is meant to encompass mature and immature animals, such as cattle, sheep, deer, goats, musk ox, buffalo, water buffalo and camels.

The present compounds are all known compounds and are disclosed in U.S. Pat. No. 3,135,594 which is incorporated herein by reference and made a part hereof. A preferred compound is 2-chloro-6-(trichloromethyl)pyridine, commonly known as nitrapyrin.

In practicing the present invention any one or more of the compounds of Formula I are orally administered to animals in a dosage form, such as, in admixture with feed, feed concentrates or supplements and additionally in the form of boluses, capsules, tablets, suspensions, emulsions or solutions containing one or more of said compounds. These dosage forms are themselves novel and constitute an embodiment of the invention.

The effective rumen-modifying amounts of the present compounds are found in the range of from about 0.1 to about 4 milligrams per kilogram of bodyweight of the animal per day (mg/kg/day). This effective range can vary depending on many factors, such as, the size of the animal, the species of the animal, the age of the animal, the particular active compound used, the dosage form employed or the particular sensitivity of the particular animal. The optimum range of an effective amount, based on variables such as those mentioned above, can be found using conventionally known techniques, i.e., dose titration determinations.

An effective rumen-modifying amount of the present compounds is ordinarily administered substantially daily to ruminants having a developed rumen function and preferably daily during the growth and/or finishing stage of commercial meat-producing ruminants in a feed lot. Alternatively, the present compounds can be administered to ruminants in the pasture. "Substantially daily" administration of the active compounds described herein is meant to encompass dosage schedules, such as, for example, every other day administration or administration 5 or 6 days in each 7 day period, as well as each and every day administration all of which are within the scope of the present invention.

The present compounds are conveniently incorporated in a standard feed composition in an appropriate amount to achieve the desired daily dosage. This amount will vary depending upon the amount of feed composition consumed daily by the animal. For example, one or a mixture of two or more of the present compounds are conveniently incorporated in a cattle feed composition at a concentration in the range of from about 3 to about 200 grams per ton of feed (3.3–220 ppm). The present compounds may also be incorporated in a mineral, protein or energy-type feed additive supplement or water supply in an appropriate amount to provide an effective rumen modifying daily dosage. Standard feed formulations are described in E. W. Crampton et al, *Applied Animal Nutrition*, W. H. Freeman and Company, San Francisco, CA., 1969 and D. C. Church, *Livestock Feeds and Feeding*, O & B Books, Corvallis, Or., 1977, both of which are incorporated herein by reference.

For commercial use, it is convenient to provide a feed additive premix, mineral supplement or concentrate containing one or more of the present compounds in a proportion such that a predetermined quantity of the premix is to be added per tone of complete feed, for example, from about 0.1 to about 1,000 pounds contains from about 3 to about 200 grams of one or a mixture of the present compounds. The feed additive premix or concentrate comprises one or more of the present compounds and a physiologically acceptable carrier such as soybean meal or ground corn or other edible feed grade material, mineral mixtures or innocuous diluent, such as, an alcohol, a glycol or molasses, physiologically suitable for the animal at hand. A concentrate may contain from about 0.001 to about 99 percent by weight of one or a mixture of two or more of the present compounds in intimate admixture with a suitable adjuvant therefor.

In further embodiments, the method of the present invention contemplates treating or dosing an animal with one of the present novel compositions containing at least one of the present compounds as the active ingredient which also can be advantageously employed in combination with one or more additional additives such as coccidiostats, antibiotics, minerals, vitamins or compatible growth promoters employed in animal husbandry.

The animal feeds most generally used in conjunction with this invention are composed of various grain and/or grain mixtures and/or roughage feeds such as hay, cotton seed hulls, rice hulls, silage, or other high fiber feedstuffs commonly fed to meat-, milk-, and/or wool-producing animals, especially in cattle or sheep feeds.

Examples of physiologically acceptable carriers for premix or concentrate compositions include soybean meal, corn oil, ground corn, ground corn cobs, barley, wheat, mineral mixtures containing, e.g., vermiculite or diatomaceous earth, corn gluten meal, corn distillers' solubles or soy flour. The active ingredient will be used in amounts to satisfy the criteria set forth above. This premix or concentrate is then in turn mixed uniformly with the normal diet for the animal as desired by the grower or the feed mixer. The above mentioned grains, grain mixtures, roughage feeds, usual additives, carriers and innocuous diluents constitute physiologically acceptable adjuvants for purposes of this invention.

The dosage of a preferred compound, 2-chloro-6-(trichloromethyl)pyridine, in cattle, falls in the range of from about 0.1 to about 4 mg/kg/day or from about 3 to about 200 grams/ton of feed (3.3–220 ppm) and preferably in the range of from about 0.2 to about 3 mg/kg/day or from about 7 to about 150 grams/ton of feed (8–165 ppm) and even more preferably in the range of from about 0.4 to about 2 mg/kg/day or from about 13.5 to about 100 grams/ton of feed (15–110 ppm).

The following examples illustrate the practice of the present invention but, as such, should not be construed as limitations upon the overall scope of the same.

EXAMPLE 1

Continuous Culture Medium

A continuous culture medium with trypticase useful for in vitro rumen fermentation tests was prepared by admixing the following ingredients:

| | |
|---|---|
| Dry nutrients | 0.8 g |
| Mineral Solution 1 | 7.5 ml |
| Mineral Solution 2 | 7.5 ml |
| Micromineral Solution | 1.5 ml |
| Resazurin Solution 0.1% | 0.1 ml |
| Clarified Rumen Fluid | 10.0 ml |
| $NaHCO_3$ 6.33% solution | 8.0 ml |
| $Na_2S.9H_2O$ 2.5% solution | 0.5 ml |
| Distilled Water | 64.9 ml |
| | 100.0 ml |

The dry nutrients comprised 0.3 g cellulose; 0.300 g Trypticase ®; 0.1 g glucose anhydrous and 0.1 g soluble starch.

The clarified rumen fluid was prepared by collecting rumen fluid from a fistulated cow on an all-roughage diet approximately 12 hours after the evening feeding. The rumen fluid was strained through 8 layers of cheese cloth and then centrifuged at $14,000 \times g$ for 30 minutes in a refrigerated high speed centrifuge. The supernatant was placed in 1 liter pyrex bottles and autoclaved 15 minutes at 16 pounds of pressure for sterilization.

The remainder of the solutions used in preparing the continuous culture medium were added as stock solutions, the ingredients of which are listed below in gram/liter of water (g/l):

| | (g/l) |
|---|---|
| Mineral Solution 1 | |
| $K_2HPO_4.3H_2O$ | 16.37 |
| Mineral Solution 2 | |
| $KH_2PO_4$ | 12.5 |
| $MgSO_4.7H_2O$ | 3.0 |
| NaCl | 12.0 |
| $CaCl_2.2H_2O$ | 1.6 |
| Resazurin Solution 0.1% | |
| Resazurin | 1.0 |
| Sodium Bicarbonate Solution 6.33% | |
| (Saturated with & stored under 100% $CO_2$) | |
| $NaHCO_3$ | 6.33 |
| Sodium Sulfide Solution 2.5% | |
| (Stored Under Nitrogen) | |
| $NA_2S.9H_2O$ | 25.0 |
| Micromineral Solution | |
| (Adjusted to pH of 2 with HCl) | |
| $FeSO_4.7H_2O$ | 0.200 |
| $H_3BO_3$ | 0.030 |
| $CoCl_2.6H_2O$ | 0.020 |
| $ZnSO_4.7H_2O$ | 0.010 |

-continued

|  | (g/l) |
|---|---|
| MnCl$_2$.4H$_2$O | 0.003 |
| Na$_2$MoO$_4$.2H$_2$O | 0.003 |
| NiCl$_2$.6H$_2$O | 0.002 |
| CuCl$_2$.2H$_2$O | 0.001 |

After preparing the above continuous culture medium enough CO$_2$ was sparged into it to lower the pH to between 6.8–7.0.

EXAMPLE 2

In Vitro Rumen Fermentation Test

To each of eight 250 ml flasks, equipped with manometers and having ports for gas and liquid sampling, was added 100 ml of fresh rumen fluid obtained from a fistulated cow on a hay diet and 100 ml of continuous culture medium of Example 1. The flasks were then sparged with CO$_2$, sealed and then placed in a shaker unit having a constant temperature of 39° C. The flasks were then placed into 4 groups of duplicates. Each day gas samples were taken from the flasks. After taking the gas samples each day, 100 ml of fluid was removed from each flask of which 20 ml was frozen for future analysis for amino nitrogen (amino-N), ammonia nitrogen (ammonia-N), acetate, propionate, butyrate, total volatile fatty acids (VFA) and isoacids content. Before freezing, the pH of the fluid was determined. After withdrawing the 100 ml sample for analysis, 100 ml of continuous culture medium of Example 1 was added to each flask. Three hours after the addition of the continuous culture medium the manometers were adjusted and the gas rate was determined over the next 2 hour period. On day 6 of the experiment 2-chloro-6-(trichloromethyl)pyridine (nitrapyrin) was added to the contents of 3 groups of flasks in the following concentrations: 2, 10 and 20 parts per million by weight (ppm). The other group served as the control group. Samples were taken daily as described above with the exception that when the continuous culture medium was added to the flask it contained nitrapyrin in a concentration corresponding to each of the 4 groups. The average data of each group is listed in Table 1. The data is reported in terms of percent of control wherein all of the data of the control group is set at 100 percent. For example, a numerical value of 200 in Table I would indicate a two-fold increase over the control. The results shown in Table I indicate that nitrapyrin decreases methane production, favorably shifts the acetate/propionate ratio and increase the level of amino acid nitrogen.

EXAMPLE 3

Ruminant Feed Containing Nitrapyrin for Cattle on an Intermediate Diet

The following ingredients constitute a typical feed for cattle on an intermediate diet:

| Ingredient | Percent by Weight of Total Feed Composition |
|---|---|
| Dehydrated Alfalfa Meal | 25.0 |
| Cottonseed Hulls | 5.0 |
| Steamrolled Corn | 60.0 |
| Soybean meal (44%) | 3.0 |
| Calcium Carbonate | 1.0 |
| Sodium Tripolyphosphate | 0.5 |
| Cane Molasses | 5.0 |
| Trace Mineral Salts | 0.5 |
| Nitrapyrin | 3–200 ppm |

The above feed is fed to cattle as an intermediate or growing diet. After the intermediate diet a finishing diet is substituted until the cattle are ready for slaughter. When the above diet is fed to cattle the feed utilization efficiency and growth rate of the cattle is improved when compared to cattle on an equivalent diet but containing no nitrapyrin.

EXAMPLE 4

Ruminant Feed Containing Nitrapyrin for Cattle on a Finishing Diet

The following ingredients constitute a typical feed for cattle on a finishing diet:

| Ingredient | Percent by Weight of Total Feed Composition |
|---|---|
| Dehydrated Alfalfa Meal | 5.0 |
| Cottonseed Hulls | 10.0 |
| Steamrolled Corn | 74.8 |
| Soybean meal (44%) | 3.0 |
| Calcium Carbonate | 0.7 |
| Sodium Tripolyphosphate | 0.3 |
| Cane Molasses | 5.0 |
| Trace Mineral Salts | 0.5 |
| Urea | 0.7 |
| Nitrapyrin | 3–200 ppm |

The above diet is fed to cattle on a finishing diet. The finishing diet is fed to the cattle until time of slaughter. When the above diet is fed to cattle the feed utilization efficiency and growth rate of the cattle is improved when compared to cattle on an identical diet but containing no nitrapyrin.

In other representative operations, various (trichloromethyl)pyridine compounds, described herein, are orally administered to ruminants whereby similar

TABLE I

| | AVERAGE DATA FOR DAYS 7-14 BASED ON PERCENT OF CONTROL | | | | | | | | | | |
|---|---|---|---|---|---|---|---|---|---|---|---|
| Group | Gas Rate | CH$_4$ | H$_2$ | Amino-N* | Ammonia-N* | Isoacids | Acetate | Propionate | Butyrate | Total VFA | Acetate Propionate |
| 1. Nitrapyrin 2 ppm | 107 | 77 | 430 | 94 | 101 | 108 | 95 | 104 | 120 | 100 | 91 |
| 2. Nitrapyrin 10 ppm | 78 | 3 | 1114 | 215 | 82 | 97 | 84 | 98 | 135 | 93 | 86 |
| 3. Nitrapyrin 20 ppm | 88 | 2 | 1284 | 360 | 70 | 78 | 78 | 53 | 114 | 73 | 148 |

*N = nitrogen

We claim:

1. A method of increasing the growth rate and/or the efficiency of feed utilization in ruminant animals having a developed rumen function which comprises the orally administering to such animals a rumen-modifying amount of one or a mixture of two or more compounds corresponding to the formula

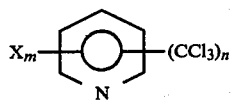

wherein
n represents 1, 2 or 3;
each X independently represents methyl or chloro;
m represents 0, 1, 2, 3 or 4 with the proviso that n+m is not greater than 5; and
physiologically acceptable salts thereof.

2. The method of claim 1 wherein said compound is 2-chloro-6-(trichloromethyl)pyridine or physiologically acceptable salts thereof.

3. The method of claim 2 wherein said ruminants are cattle.

4. The method of claim 2 wherein said ruminants are sheep or goats.

5. The method of claim 2 wherein said compound is administered to said ruminants at a rate of from about 0.1 mg/kg bodyweight/day to about 4 mg/kg bodyweight/day.

6. The method of claim 2 wherein said compound is administered to said ruminants at a rate of from about 0.2 mg/kg bodyweight/day to about 3 mg/kg bodyweight/day.

7. The method of claim 2 wherein said compound is administered to said ruminants at a rate of from about 0.4 mg/kg bodyweight/day to about 2 mg/kg bodyweight/day.

8. The method of claim 2 wherein said compound is administered to said ruminants by incorporating said compound into a ruminant feed at a concentration of from about 3 ppm to about 220 ppm based upon the total weight of the feed.

9. The method of claim 8 wherein said ruminants are cattle.

10. The method of claim 8 wherein said ruminants are sheep or goats.

11. A ruminant feed comprising
(a) a standard ruminant feed, and
(b) an effective rumen-modifying amount of one or a mixture of two or more compounds corresponding to the formula

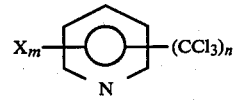

wherein
n represents 1, 2 or 3;
each X independently represents methyl or chloro;
m represents 0, 1, 2, 3 or 4 with the proviso that m+n is not greater than 5; and
physiologically acceptable salts thereof.

12. The ruminant feed of claim 11 wherein said compound is 2-chloro-6-(trichloromethyl)pyridine or physiologically acceptable salts thereof.

13. The ruminant feed of claim 12 wherein said compound is present in said feed in an amount of from about 3 to about 200 parts per million by weight.

14. The ruminant feed of claim 11 which when fed to a ruminant provides to the ruminant from about 0.1 to about 4 milligrams per kilogram of bodyweight per day of one or more of said compounds.

15. The ruminant feed of claim 14 wherein said compound is 2-chloro-6-(trichloromethyl)pyridine or physiologically acceptable salts thereof.

16. A ruminant feed concentrate comprising:
(a) a standard ruminant feed, and
(b) an effective rumen-modifying amount of one or a mixture of two or more compounds described in claim 1.

17. The ruminant feed concentrate of claim 16 which comprises from about 0.5 to about 99 percent by weight of said active compound.

18. The ruminant feed concentrate of claim 17 wherein said active compound is 2-chloro-6-(trichloromethyl)pyridine or physiologically accetable salts thereof.

* * * * *